United States Patent
Cho et al.

(10) Patent No.: US 9,700,531 B2
(45) Date of Patent: Jul. 11, 2017

(54) COMPOSITION COMPRISING METFORMIN AS ACTIVE INGREDIENT FOR PREVENTING OR TREATING INFLAMMATORY BOWEL DISEASE

(71) Applicant: CATHOLIC UNIVERSITY INDUSTRY ACADEMIC COOPERATION FOUNDATION, Seoul (KR)

(72) Inventors: Mi-La Cho, Seoul (KR); Seon-Yeong Lee, Suwon-si (KR); Eun-Ji Yang, Seoul (KR); Hye-Jin Son, Seoul (KR); Eun-Kyung Kim, Seoul (KR); Jun-Geol Ryu, Taebaek-si (KR)

(73) Assignee: Catholic University Industry Academic Cooperation Foundation, Seoul (KR)

( * ) Notice: Subject to any disclaimer, the term of this patent is extended or adjusted under 35 U.S.C. 154(b) by 0 days.

(21) Appl. No.: 14/663,235

(22) Filed: Mar. 19, 2015

(65) Prior Publication Data
US 2015/0196511 A1    Jul. 16, 2015

Related U.S. Application Data

(63) Continuation-in-part of application No. PCT/KR2013/008428, filed on Sep. 17, 2013.

(30) Foreign Application Priority Data

Sep. 21, 2012  (KR) .......................... 10-2012-0104969
Sep. 17, 2013  (KR) .......................... 10-2013-0111679

(51) Int. Cl.
| A61K 31/155 | (2006.01) |
| A61K 38/17 | (2006.01) |
| A61K 39/395 | (2006.01) |
| A61P 37/02 | (2006.01) |
| A61K 45/06 | (2006.01) |

(52) U.S. Cl.
CPC ........ *A61K 31/155* (2013.01); *A61K 38/1793* (2013.01); *A61K 45/06* (2013.01)

(58) Field of Classification Search
CPC .......................... A61K 31/155; A61K 38/1793
USPC .......................................................... 514/635
See application file for complete search history.

(56) References Cited

U.S. PATENT DOCUMENTS

| 2002/0142993 A1 | 10/2002 | Gaddam |
| 2009/0143442 A1 | 6/2009 | Colca |
| 2011/0294852 A1 | 12/2011 | Hojgaard |
| 2015/0238445 A1* | 8/2015 | Cho ..................... A61K 31/155 435/377 |

FOREIGN PATENT DOCUMENTS

| WO | 2011/056590 A1 | 5/2011 |
| WO | 2013/079721 A1 | 6/2013 |

OTHER PUBLICATIONS

Li et al. Heart Vessels 2009, 24, 446-453.*
Wullaert et al. Cell Research 2011, 21 (1), 146-158.*
Abraham et al. The New England Journal of Medicine 2009, 361 (21), 2066-2078.*
Nanda et al. Expert Opinion Pharmacotherapy 2004, 5(5), 1175-1186, Abstract.*
Nath et al. J. Immunol. 2009, 182 (12), 8005-8014.*
Talley et al. The American Journal of Gastroenterology 2011, 106, Suppl. 1, S2-S25.*

* cited by examiner

*Primary Examiner* — Irina Neagu
(74) *Attorney, Agent, or Firm* — Joseph Hyosuk Kim; JHK Law

(57) ABSTRACT

The present invention relates to a composition comprising metformin as an active ingredient for preventing or treating inflammatory bowel disease. The metformin compound or the metformin-etanercept (product name: Enbrel) composite according to the present invention may have excellent effects of maintaining the thickness of the small intestine and length of the large intestine normal, inhibiting or decreasing the activity of IL-17 and TNF-a, and promoting or increasing the activity of IFNr, and therefore can be effectively used as a pharmaceutical composition for preventing or treating autoimmune diseases including inflammatory bowel disease.

2 Claims, 10 Drawing Sheets

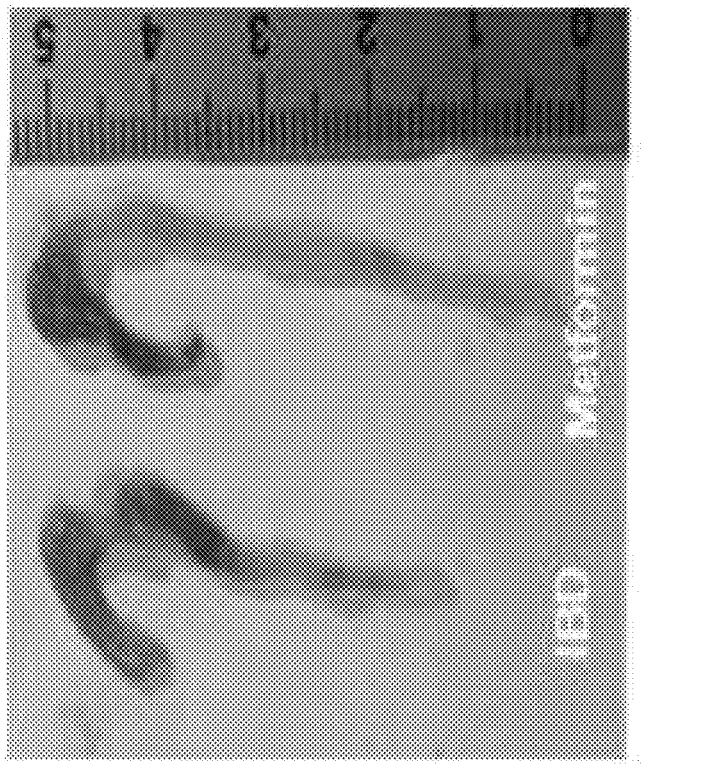
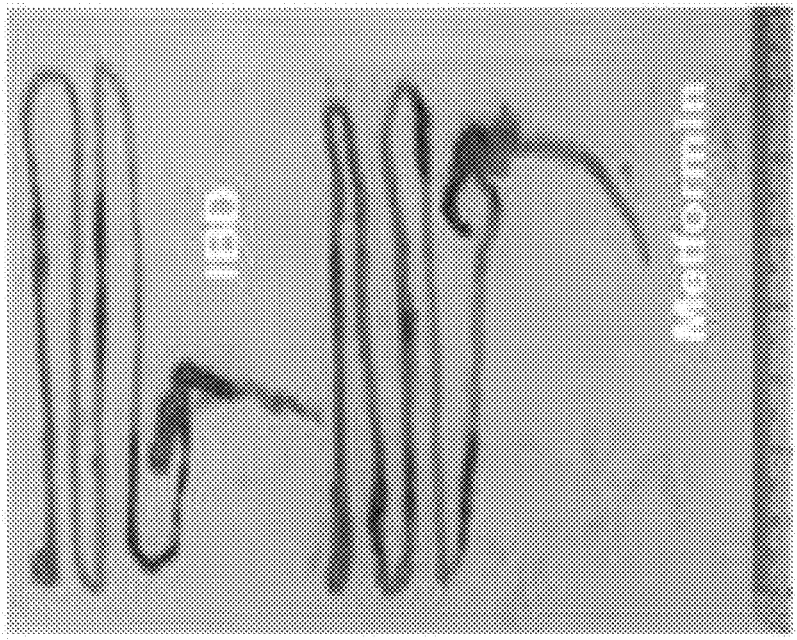
Fig. 2

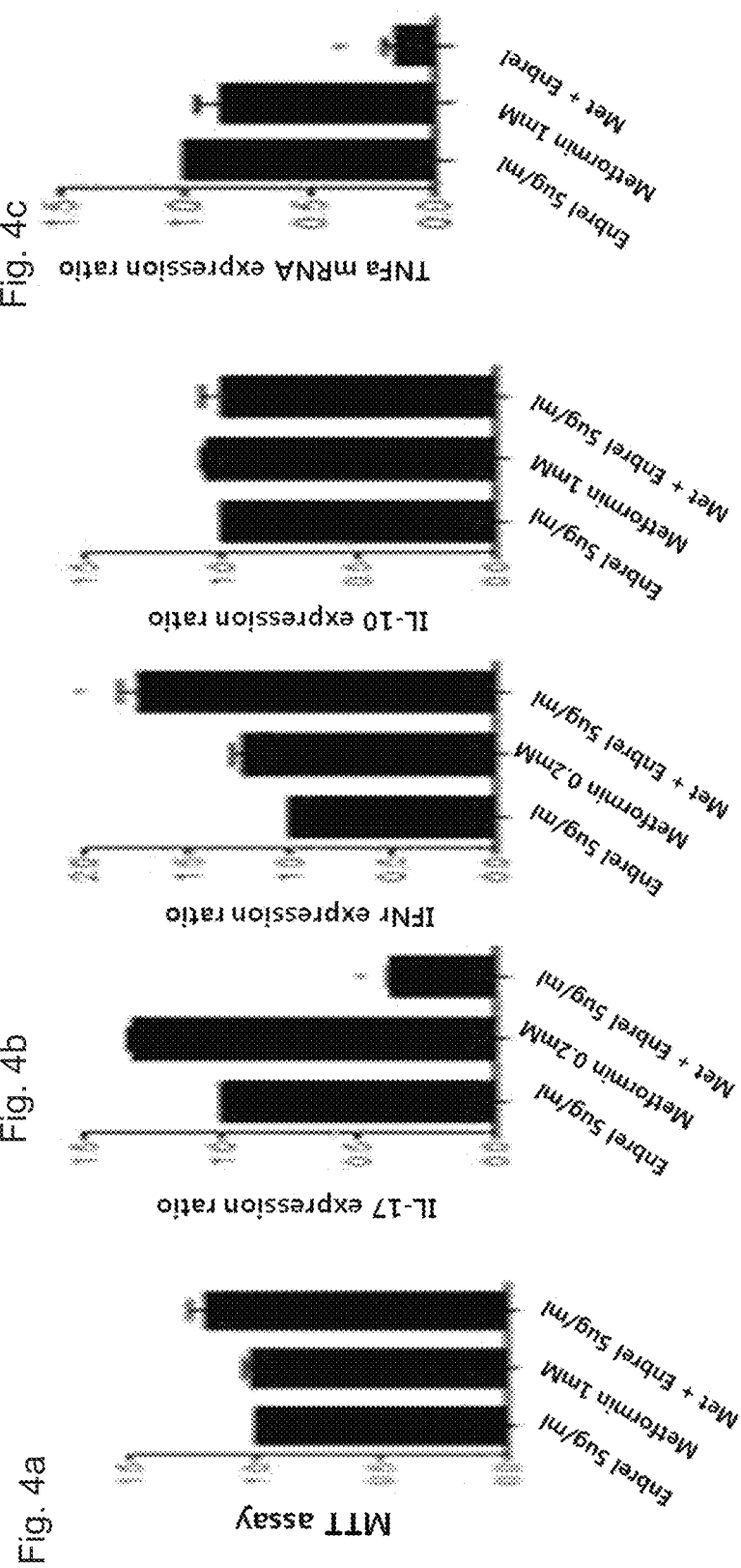

COMPOSITION COMPRISING METFORMIN AS ACTIVE INGREDIENT FOR PREVENTING OR TREATING INFLAMMATORY BOWEL DISEASE

This application is a Continuation in part of International Application No. PCT/KR2013/008428 filed on 17 Sep. 2013, which claims priority from Korean Patent Application No. 10-2012-0104969, filed on 21 Sep. 2012, and 10-2013-0111679, filed on 17 Sep. 2013.

TECHNICAL FIELD

The present invention relates to a composition including Metformin as an active ingredient for preventing or treating an inflammatory bowel disease.

BACKGROUND ART

An inflammatory bowel disease is a disease that causes the chronic inflammation of unknown etiology into intestines and it can be classified into ulcerative colitis and a Crohn's disease. The ulcerative colitis is a disease causing the continuous development of erosion or ulcer on a colonic mucosa and causes hematochezia, mucous and bloody stool, diarrhea, and abdominal pain, and if severe, the systemic symptoms, such as, fever, weight loss, and anemia, may occur. Moreover, the Crohn's disease is a disease that causes the lesions, such as, ulcer, in a discontinuous way on random sites of the digestive tract from mouth to anus, and along with abdominal pain, diarrhea and hematochezia, it causes the symptoms, such as, fever, weight loss, lethargy, and anemia, if it is severe. Both the ulcerative colitis and Crohn's disease are a chronic intractable disease, in which the symptoms are temporarily improved, but repeatedly recur. Although neither the cause nor patho-physiology of the inflammatory bowel disease was clearly identified yet, it is estimated that the genetic factors, the environmental factors, such as, intestinal bacteria or food, and the immunological factors are involved in combination in the pathogenesis.

In the past, it was known that westerners are more prone to have ulcerative colitis and Crohn's disease, but due to the change of life habit such as eating habits, the number of patient is dramatically increasing in Asia including South Korea. Nevertheless, due to uncertain etiology, the fundamental methods of treatment have not been established yet and therefore, some drugs are currently being used that are only able to delay and palliate the progression of symptoms and prolong such states as long as possible but not able to aim for complete treatment. As drugs for such conservative therapy, an aminosalicylic acid, adrenocortical steroid, immunosuppressant, and a TNF-α monoclonal antibody are mainly used, but a number of side effects are being reported. For instance, the side effects, such as. nausea, vomiting, loss of appetite, rash, headache, hepatic dysfunction, leucopenia, abnormal erythrocyte, proteinuria and diarrhea are being reported for sulfasalazine that is frequently used as aminosalicylic acid. Prednisolone, which is an adrenocortical steroid is used by oral administration, enema, suppository and intravenous injection, but has intense side effects such as gastric ulcer or necrosis of the femoral head caused by long-term use. Although Inflixima, a TNF-α monoclonal antibody, was approved by FDA of the United States in 1998 as a treatment for Crohn's disease and used to treat patients with Crohn's disease, side effects such as pancytopenia, drug induced lupus, hepatitis B and reactivated tuberculosis are occurring. Also the U.S FDA is warning physicians that risk of lymphoma and other types of cancers can be increased, if Infliximab and other types of Tumor Necrosis Factors (TNF) are used.

Therefore, the development of new treatment for an inflammatory bowel disease that is more effective, safer and has fewer side effects than currently available treatments for an inflammatory bowel disease is urgently needed.

DISCLOSURE

Technical Problem

Therefore, the inventors of the present invention identified that the Metformin compound or the Metformin-Etanercept (product name: Enbrel®) composite can be used for the prevention or treatment of an inflammatory bowel disease by identifying that they have an effect on maintaining the thickness of the small intestine and length of the large intestine in a normal state, inhibiting or decreasing the activities of IL-17 and TNF-α and promoting or increasing the activity of IFNr. Therefore, the inventors completed the present invention.

Hence, an objective of the present invention is directed to providing a composition including a Metformin compound or a pharmaceutically acceptable salt thereof as an active ingredient for prevention or treatment of an inflammatory bowel disease.

Technical Solution

In order to achieve the objective, the present invention provides a composition including a Metformin compound or a pharmaceutically acceptable salt thereof as an active ingredient for the prevention or treatment of an inflammatory bowel disease.

In one exemplary embodiment of the present invention, the composition may further include a TNF-α inhibitor.

In one exemplary embodiment of the present invention, the composition may further include Etanercept.

In one exemplary embodiment of the present invention, the composition may have an effect on maintaining the thickness of small intestine and length of large intestine in a normal state.

In one exemplary embodiment of the present invention, the composition may inhibit or decrease the activity of IL-17, promote or increase the activity of IFNr, and inhibit or decrease the expression of TNF-α.

In one exemplary embodiment of the present invention, the inflammatory bowel disease may be selected from the group consisting of a Crohn's disease, intestinal lesions concomitant with a Behcet's disease, ulcerative colitis, hemorrhagic rectal ulcer, and pouchitis.

Advantageous Effects

The Metformin compound or the Metformin-Etanercept composite of the present invention can be useful as a pharmaceutical composition for the prevention or treatment of the autoimmune diseases including an inflammatory bowel disease as they have excellent effect on maintaining the thickness of the small intestine and length of the large intestine in a normal state, inhibiting or decreasing the activity of IL-17 and TNF-α, and promoting or increasing the activity of IFNr.

DESCRIPTION OF DRAWINGS

FIG. 2 illustrates the results of measuring the thicknesses of the small intestines and lengths of the large intestines for the experimental animals, which were divided into an inflammatory bowel disease-induced animal model group and an inflammatory bowel disease-induced animal model group, which was administered with Metformin.

FIG. 4a illustrates the results of analyzing whether there were cytotoxicities through a MTT assay for the group, in which the spleen cells of a normal mouse group were treated with Metformin, the group treated with Etanercept (Product Name: Enbrel®), and the group treated with the Metformin-Etanercept (Product Name: Enbrel®) composite.

FIGS. 4b and 4c illustrate the results of measuring the expression levels of the inflammatory cytokines by an ELISA technique for the group, in which the spleen cells of a normal mouse group were treated with Metformin, the group treated with Etanercept (Product Name: Enbrel®), and the group treated with the Metformin-Etanercept (Product Name: Enbrel®) composite.

MODES OF THE INVENTION

Figure 1A:
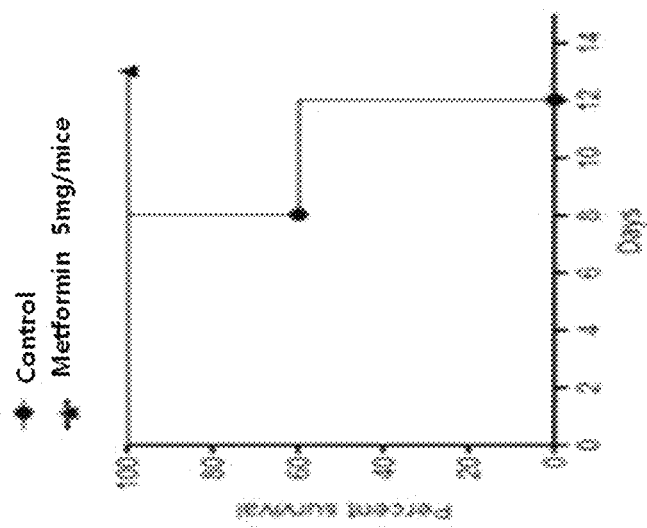
FIGS. 1A-1C illustrate the results of measuring the weights and survival rates of the experimental animals, which were divided into an inflammatory bowel disease-induced animal model group, and an inflammatory bowel disease-induced animal model group, which was administered with Metformin.

The present invention relates to a composition including a metformin compound or a pharmaceutically acceptable salt thereof as an active ingredient for preventing or treating an inflammatory bowel disease.

The present invention identified for the first time that the metformin compound or the metformin-etanercept (product name: Enbrel®) composite has excellent effect on maintaining the thickness of the small intestine and the length of the large intestine in a normal state, inhibiting or decreasing the activity of IL-17 and TNF-α, and promoting or increasing the activity of IFNr and therefore, it is to provide the metformin compound of the present invention as a composition for prevention or treatment of inflammatory bowel disease.

The inventors of the present invention paid attention to the metformin compound of the present invention while studies on new compounds for prevention or treatment of inflammatory bowel disease were being conducted and Metformin is known to be effective in treating diabetes. Furthermore, although it is described in Korean Patent No. 2009-0005513 that Metformin malonate has an anti-diabetic activity, no reports were made regarding the fact that Metformin is used for the prevention and treatment of an inflammatory bowel disease.

Although the cause of an inflammatory bowel disease is not yet concretely proven, it is presumed to be related to the immune function of intestine and besides, genetic factor, intestinal microbial infection hypothesis, psychological factor and other various factors are thought to be involved in combination. The pathophysiology of an inflammatory bowel disease can be divided into initiation, induction, perpetuation, and amplification process of non-specific inflammatory response and amplification process refers to a process in which tissue damages and clinical symptoms are caused by inflammatory response that was not properly reduced due to the defects of immunoregulation. The initiation and continuation of inflammation may be independent and a number of abnormal immunoregulation can bring about similar results because the non-specific final routes causing tissue damages are identical. The cytokines that regulate immune responses are released from activated T lymphocytes and depending on their function, they can be classified into T-helper 1 (IL-12, interferon-) and T-helper 2 (IL-4, IL-5, IL-10, IL-13). Th1 regulates cellular immune responses and Th2 regulates humoral immune responses. Recently it was hypothesized that ulcerative colitis is a disease induced by Th2 response, while Crohn's disease is induced by Th1 response. Meanwhile, the research group of Dr. Arian Laurence at U.S National Institute of Health reported that production of IL-17 is interfered and autoimmune responses related to the defects of IL-2 is alleviated, if STAT3 gene, a transcription factor, is removed from T cell (Nature Immunology 2011, 12 (3):247) and thus, it was learned that interleukin 2 (IL-2) is a cytokine involved in human autoimmune diseases and restricts the production of IL-17.

Figure 1B:
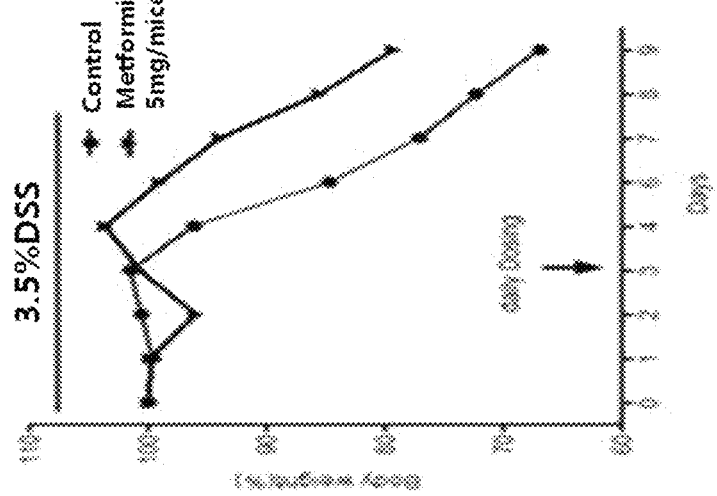

In this sense, the inventors of the present invention investigated whether the metformin compound inhibits inflammatory cytokine and has actual effectiveness in treatment of an inflammatory bowel disease and according to one exemplary embodiment of the present invention, when the weights and survival rates of experimental animals were measured after dividing the groups into an animal model group with an inflammatory bowel disease and an animal model group with an inflammatory bowel disease administered with Metformin for which 5 mg of Metformin was orally administered 3 days after the disease was induced, the increase in weights (see FIGS. 1a and 1b) and higher survival rates (see FIG. 1c) were observed in the group administered with Metformin in comparison to the animal models with an inflammatory bowel disease, the control group. Based on the histological findings, small intestine of animal models of inflammatory bowel disease, which is the control group were observed to be narrower than the group treated with Metformin and particularly for large intestine, shortened length was observed (see FIG. 2).

Etanercept (product name: Enbrel®), as one type of immunosuppressant, is an antagonist of a substance named TNF (Tumor Necrotic Factor) and is a drug commonly used to treat rheumatoid arthritis, psoriasis, ankylosing spondylitis, and an inflammatory bowel disease.

Figure 3A:
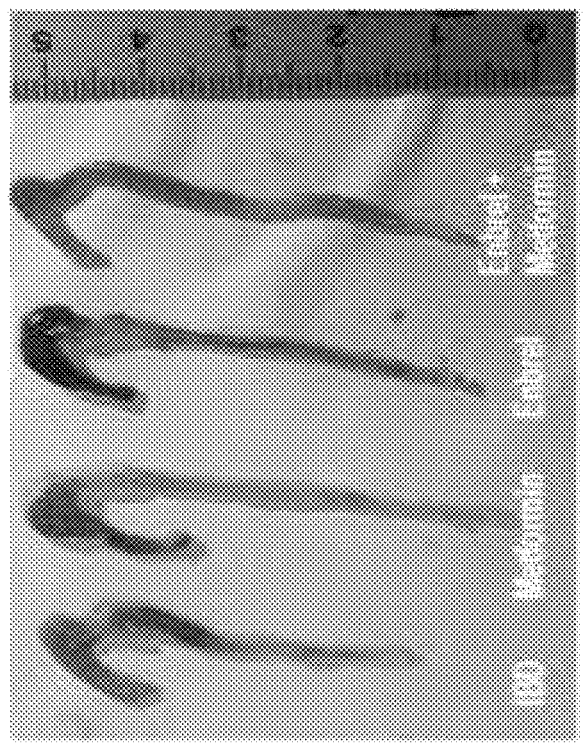
FIGS. 3A-3B illustrate the results of measuring the thicknesses of the small intestines and the lengths of the large intestines for the animal model groups, which were divided into an inflammatory bowel disease-induced animal model group as a control group, the group, in which to the spleen cells of the inflammatory bowel disease-induced mice were treated with Metformin, the group treated with Etanercept (Product Name: Enbrel®), and the group treated with a Metformin-Etanercept (Product Name: Enbrel®) composite.
Figure 3B:
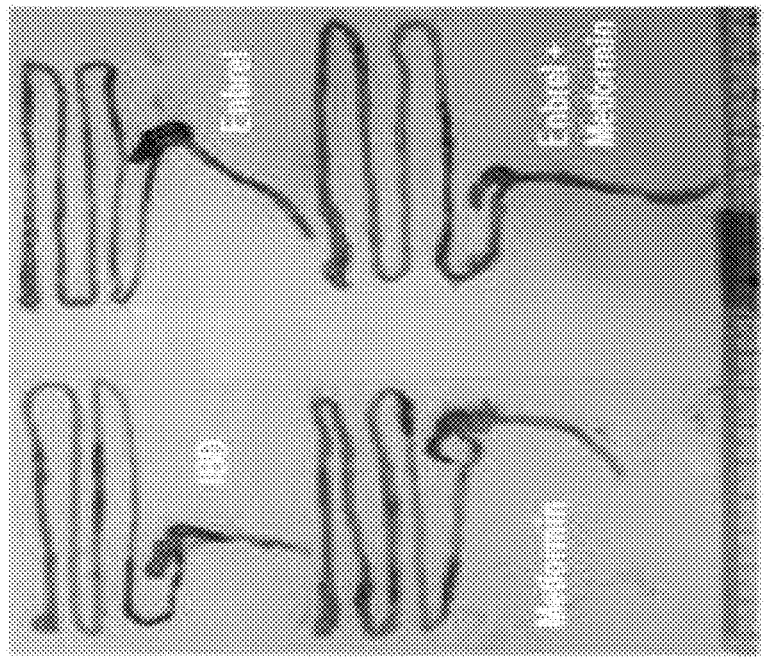

In this regard, in the present invention, it was identified that if the Metformin compound is concomitantly treated with Etanercept (Product Name: Enbrel®) in order to eliminate the side effects of Etanercept (Product Name: Enbrel®) and maximize the efficacy, the thickness of small intestine becomes thicker than that of the group treated solely with Metformin and Etanercept (Product Name: Enbrel®) (see FIG. 3) and accordingly, it is effective in treatment of an inflammatory bowel disease and the expressions of IL-17 and TNF-α were inhibited more considerably and IFNr was increased more in the group treated with the Metformin-Etanercept (Product Name: Enbrel®) composite than in the group treated solely with Enbrel® and Metformin (see FIG. 4).

Figure 5:
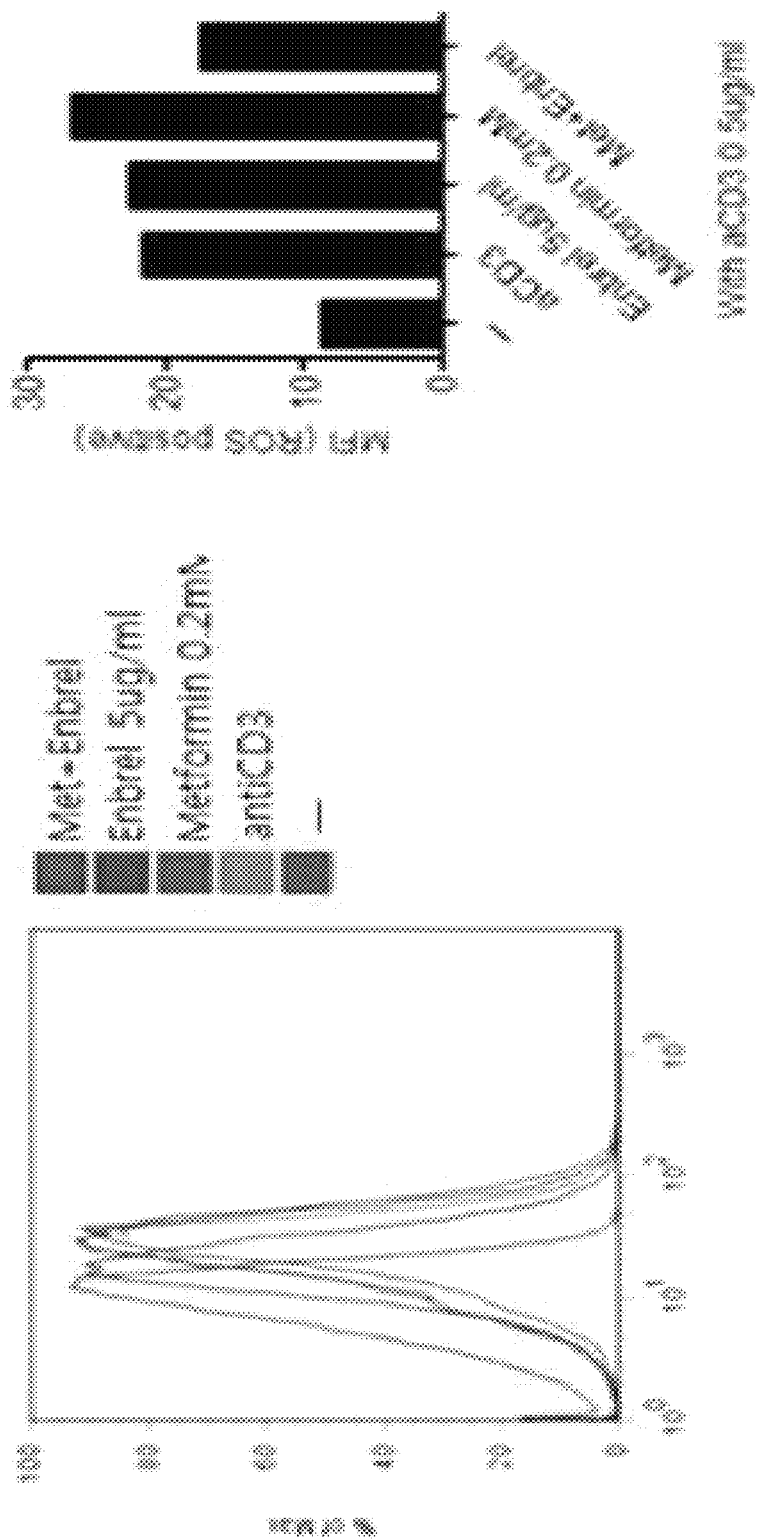
FIG. 5 illustrates the results of measuring the following cells by FACs after collecting the cells from the group, in which the spleen cells of a normal mouse group were treated with Metformin, the group treated with Etanercept (Product Name: Enbrel®), and the group treated with the Metformin-Etanercept (Product Name: Enbrel®) composite, and then, reacting the cells with a ROS antibody with a FITC wavelength range.

Furthermore, after treating the spleen cells of a normal mouse group solely with Metformin and Etanercept (Product Name: Enbrel®) and with the Metformin-Etanercept (Product Name: Enbrel®) composite, the inventors of the present invention collected each cell, reacted those cells with an ROS antibody with a FITC wavelength range and measured the cells using Fluorescence activated cell sorting (FACs) in order to identify whether the Metformin-Etanercept (Product Name: Enbrel®) composite of the present invention is capable of inhibiting ROS, an important factor known to be involved in a number of autoimmune inflammatory responses and consequently, it was identified that ROS is significantly inhibited by the Metformin-Etanercept (Product Name: Enbrel®) composite, while no ROS inhibitory effect was observed when only Etanercept (Product Name: Enbrel®) or Metformin was treated (see FIG. 5).

Therefore, from the above results, the inventors of the present invention identified that the Metformin compound or the Metformin-Etanercept (Product Name: Enbrel®) composite can effectively inhibit an inflammatory bowel disease and furthermore, it can be used for treating the autoimmune diseases.

Hence, the present invention can provide a composition including a Metformin compound or a pharmaceutically acceptable salt thereof as an active ingredient for preventing or treating an inflammatory bowel disease.

The Metformin compound of the present invention may be a compound described by the following Chemical Formula 1.

[Chemical Formula 1]

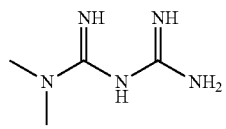

Furthermore, the compound of the present invention that is represented by Chemical Formula 1 may be used as a salt, and preferably as a pharmaceutically acceptable form of salts. As the salts, the acid addition salts that are formed by pharmaceutically acceptable free acids are preferable and as the free acids, the organic acids and inorganic acids may be used. The organic acids include a citric acid, an acetic acid, a lactic acid, a tartaric acid, a maleic acid, a fumaric acid, a formic acid, a propionic acid, an oxalic acid, a trifluoroacetic acid, a benzoic acid, a gluconic acid, a metasulfonic acid, a glycolic acid, a succinic acid, a 4-toluene sulfonic acid, a glutamic acid and an aspartic acid, but not limited thereto. Moreover, the inorganic acids include a hydrochloric acid, a bromic acid, a sulfuric acid, and a phosphoric acid, but not limited thereto.

The compound of the present invention may be isolated from the nature or the compounds produced by the method of chemical synthesis known in the related art may be used.

The inflammatory bowel disease of the present invention refers to the chronic inflammation generated in the intestine with unknown origin and although it commonly refers to ulcerative colitis and a Crohn's disease that are an idiopathic inflammatory bowel disease, it may also include an intestinal Behcet's disease, which is relatively common in Korea. In a broader sense, it also refers to infectious enteritis such as bacterial, viral, amoebic, tuberculous enteritis and any inflammatory diseases that occur in the intestine such as acute mesenteric ischemia and radiation enteritis.

Therefore, the composition of the present invention may be used as a pharmaceutical composition for preventing or treating an inflammatory bowel disease.

Unless stated otherwise, the treatment refers to the reversing, relieving, inhibiting or preventing of the disorders or diseases, or at least more than one symptom of the disorders or diseases, to which the above term is applied, and the term "treatment" refers to the act of treating when the "treatment" is defined as above. Therefore, the treatment or therapy of an inflammatory bowel disease for mammals may include more than one provided below.

(1) Inhibiting the growth of an inflammatory bowel disease, namely, the development thereof.
(2) Preventing the spread of an inflammatory bowel disease, namely, the metastasis.
(3) Relieving an inflammatory bowel disease.
(4) Preventing the recurrence of and inflammatory bowel disease, and
(5) Palliating the symptoms of an inflammatory bowel disease The composition of the present invention for the prevention or treatment of an inflammatory bowel disease may solely include the compound represented by Chemical Formula 1 or a salt thereof in a pharmaceutically effective amount or may include one or more pharmaceutically acceptable carriers, excipients, or diluents.

The pharmaceutically effective amount refers to an amount sufficient to prevent, improve and treat the symptoms of an inflammatory bowel disease.

The pharmaceutically effective amount of the Metformin compound or the salt thereof according to the present invention is 0.5 to 100 mg/day/kg, and preferably 0.5 to 5 mg/day/kg. However, the pharmaceutically effective amount may vary depending on the severity of an inflammatory bowel disease, patient's age, weight, health state, gender, the route of administration, and the treatment period.

Moreover, the "pharmaceutically acceptable" refers to a composition that is physiologically acceptable and does not cause an allergic reaction, such as, gastroenteric trouble and dizziness or responses similar to such when it is administered to human. As examples of the carriers, excipients and diluents, there are lactose, dextrose, sucrose, sorbitol, mannitol, xylitol, erythritol, maltitol, starch, acacia rubber, alginate, gelatin, calcium phosphate, calcium silicate, cellulose, methyl cellulose, polyvinyl pyrrolidone, water, methylhydroxybezoate, propyl hydroxybenzoate, talc, magnesium stearate, and mineral oils. Moreover, fillers, anti-clumping agents, lubricants, wetting agents, spices, emulsifying agents, and preservatives may be included in addition.

Furthermore, the composition of the present invention may be formulated by the known methods in the related arts so as to provide the rapid, continued or delayed excretion of an active ingredient after being administered to the mammals. The formulation may be powders, granules, tablets, emulsions, syrups, aerosols, soft or hard gelatin capsules, sterilized injection solution, and sterilized powder.

Moreover, the composition of the present invention for the prevention or treatment of an inflammatory bowel disease may be administered via various routes including oral, percutaneous, subcutaneous, intravenous, or intramuscular; the dose of an active ingredient may be adequately determined according to a number of factors, such as, the route of administration, patient's age, gender, weight, and severity of patient; and the composition of the present invention for the prevention or treatment of an inflammatory bowel disease may be administered in combination with the compounds that are known to have the effects on preventing, improving or treating the symptoms of an inflammatory bowel disease.

Therefore, the present invention can provide a drug including the composition of the present invention that includes the Metformin compound or a salt thereof as an active ingredient for the prevention or treatment of an inflammatory bowel disease and furthermore, the present invention can provide a composition including the Metformin compound or a salt thereof as an active ingredient for the treatment of an inflammatory bowel disease.

Meanwhile, the present invention can provide a food composition including the Metformin compound or a salt thereof as an active ingredient for the improvement or prevention of the symptoms of an inflammatory bowel disease and the food composition of the present invention may be used as foods that are effective for the improvement or prevention of the symptoms of an inflammatory bowel disease, such as, main ingredients and supplementary ingredients of foods, food additives, and functional foods or beverages.

The food stated herein refers to the natural or processed products that include one or more than one nutrients, preferably it refers to those that are already processed to some extent and so are in an edible state, and generally, foods, food additives, functional foods, and beverages are all included.

For the foods, in which the food composition of the present invention can be added, there are for example, all sorts of foods, beverages, gums, tea, vitamin complex, and functional foods. Additionally, the food of the present invention includes special nutrient food (for example, milk formulas, baby food), processed meat products, fish products, tofu, jellied foods, noodles (for example, ramen, noodles), bakery products, health functional foods, seasoning foods (soy sauce, soy bean paste, fermented red pepper-soybean paste, mixed paste), sauces, cookies (for example, snack types), candies, chocolates, gums, ice creams, dairy products (for example, fermented milk, cheese), other processed foods, Kimchi, salted vegetable foods (all sorts of Kimchi, pickles), beverages (for example, fruit juice, vegetable juice, soymilk, fermented beverages), and natural seasonings (for example, ramen seasoning), but not limited thereto. The foods, beverages, or food additives can be prepared by the common preparing method.

Furthermore, the functional food refers to a group of foods, in which physical, biochemical, and biotechnological techniques are used to add the value to the foods in order to enable the function of the foods to act and be manifested for specific purpose or it refers to processed foods that are designed to sufficiently express in vivo regulatory functions of the food composition regarding biological defense rhythm, disease prevention and recovery and specifically, these may be health functional foods. For the functional foods, nutritionally acceptable food supplementary additives can be included and proper carriers, excipients and diluents that are commonly used in preparation of functional foods can be included as well.

The beverage of the present invention collectively refers to any beverage to drink in order to quench thirst or to enjoy the flavor and it includes functional beverages. Except that the composition for improvement or prevention of symptoms of the immune disease should be included as an essential component in a specified ratio, there is no particular restrictions imposed on other ingredients and as in common beverages, various flavoring agents or natural carbohydrates can be added as additional ingredients.

Furthermore, besides what was described above, the food of the present invention including food composition for the improvement or prevention of an inflammatory bowel disease may include various nutritional supplements, vitamins, minerals (electrolytes), flavoring agents such as synthetic and natural flavoring agents, coloring agents, fillers (cheese and chocolate), pectic acid and its salts, alginic acid and its salts, organic acids, protective colloids, thickeners, pH adjusters, stabilizers, preservatives, glycerin, alcohol, and carbonating agents used for carbonated beverages, and these ingredients may be used independently or in combination.

For the food including the food composition of the present invention, the amount of the composition of the present invention may be 0.001 wt % to 90 wt %, and preferably 0.1 wt % to 40 wt % with respect to the total weight of the foods, and in the case of beverages, although 0.001 g to 2 g, and preferably 0.01 g to 0.1 g may be included with respect to 100 ml, it is possible to be below the above-described range in case of long-term intake with the purpose of health and hygiene or health management. Since the active ingredient is all good in terms of safety, an amount more than the above range may be used, and thus, it is not limited to thereto.

Hereinafter, the present invention will be described in detail with reference to Examples. The following Examples are only for illustrating the present invention in more detail, and it is apparent for ordinary skill in the related art that the scope of the present invention is not limited to these Examples.

Modes of the Invention

Example 1

Preparation of Animal Model of Inflammatory Bowel Disease

The inventors of the present invention first prepared the animal model with an inflammatory bowel disease in order to identify whether the Metformin of the present invention can treat an inflammatory bowel disease. For an experimental animal, a C57BL/6(H-2kb) mouse was used, and to prepare the animal model with an inflammatory bowel disease, the mouse taken with 3.5% dextran sulfate sodium (DSS) water for a week to prepare an animal model with an inflammatory bowel disease.

Example 2

Treatment Effect of Metformin on Inflammatory Bowel Disease

The inventors divided the experimental animals into an inflammatory bowel disease-induced animal model group, and an inflammatory bowel disease-induced animal model group, which was administered with Metformin, and for the group being administered with Metformin, 5 mg of Metformin was orally administered at 3 days after the disease was induced.

Figure 1C:
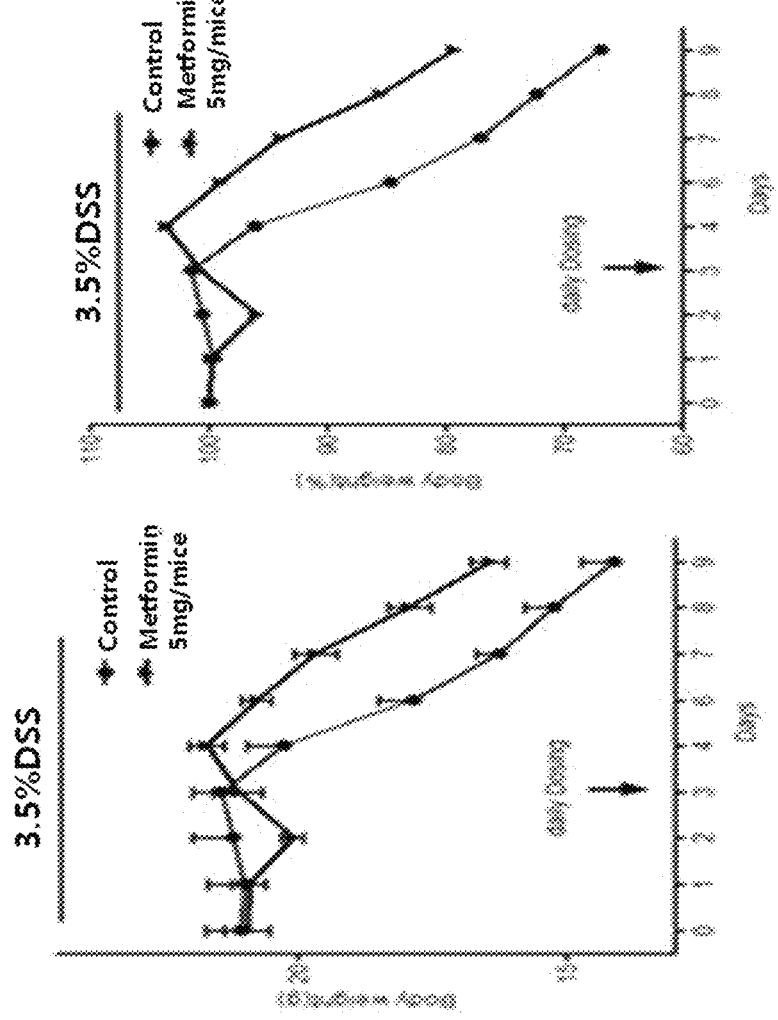

When the weights and survival rates of the experimental animals were measured, the weights of the group being administered with Metformin were determined to be 25 to 30% higher than the inflammatory bowel disease-induced animal model, the control group (see FIGS. 1a and 1b), and in contrast to the control group for which the low survival rate was observed, 100% survival rate was observed for the group being administered with Metformin (see FIG. 1c).

Moreover, based on histological findings, the small intestines of the animal model with an inflammatory bowel disease, which was the control group, were observed to be narrower than the group treated with Metformin and particularly for the large intestine, the shortened length was observed (see FIG. 2).

Therefore, the inventors of the present invention identified that Metformin of the present invention is effective for the prevention and treatment of an inflammatory bowel disease.

Example 3

Analysis of Effect of Combined Treatment of Metformin and Etanercept on the Treatment of Inflammatory Bowel Disease The inventors used the experimental animal of Example 1 as a control group in order to analyze the treatment effect for an inflammatory bowel disease by the combined treatment of Metformin with Etanercept (Product Name: Enbrel®) as an effective method of treating an inflammatory bowel disease, and the thickness of intestine and length of colon were measured for the Metformin group, in which 5 mg of Metformin was orally administered at 3 days after the disease was induced, the Etanercept group, in which 100 μg of Etanercept (Product Name: Enbrel®) was subcutaneously administered at 3 days after the disease was induced, and for the Metformin-Etanercept composite group, in which the Metformin-Etanercept (Product Name: Enbrel®) composite was administered at 3 days after the disease was induced.

As a result, in comparison with the control group, the thickness of the intestine of the group treated with Metformin and Etanercept (Product Name: Enbrel®) was determined to be thicker and became further thicker in the Metformin-Etanercept (Product Name: Enbrel®) composite group (see FIG. 3).

Example 4

Analysis of Effect of Combined Treatment of Metformin and Etanercept on Inflammatory Cytokine Inhibition The inventors treated Metformin and the Metformin-Etanercept (Product Name: Enbrel®) composite to the cells of the normal mouse group to identify the effects of Etanercept (Product Name: Enbrel®) and Metformin on the expression of cytokine. Most of all, from the observation of toxic effects of these reagents, it was known that no toxic effects could be conferred at the treated concentration of the present invention (see FIG. 4), and using an ELISA technique, IL-17, IFNr, and IL-10 in the culture media collected at 3 days after the treatment of reagent were measured.

As a result, it was identified that both Etanercept (Product Name: Enbrel®) and Metformin were effective in inhibiting the expression of IL-17 and when Etanercept (Product Name: Enbrel®) was treated in combination with Metformin, the expression of IL-17 was more significantly inhibited than when it was solely treated with Etanercept (product name: Enbrel®) and Metformin. On the other hand, IFNr was observed to have a tendency to increase when Etanercept (Product Name: Enbrel®) was treated in combination with Metformin and had no influence on the expression of IL-10 and it was known that the combined treatment of Etanercept (product name: Enbrel®) and Metformin inhibits the expression of TNF-α more significantly than Etanercept (product name: Enbrel®), which was known as a TNF-α inhibitor (see FIGS. 4b and 4c).

Therefore, it was identified that the Metformin-Etanercept (Product Name: Enbrel®) composite of the present invention could be applied to an autoimmune diseases mediated by the activity of IL-17, including an inflammatory bowel disease because the composition of the present invention could inhibit and regulate IL-17, and also activate IFN-r.

Example 5

Analysis of Antioxidant Effect of Combined Treatment of Metformin and Etanercept The oxidative stress was known to be an important factor involved in the inflammatory responses of various autoimmune diseases. Therefore, in order to identify whether the Metformin-Etanercept (Product Name: Enbrel®) composite of the present invention was capable of inhibiting ROS, an oxidative stress factor, the spleen cells of a normal mouse group was treated with Metformin, Etanercept (Product Name: Enbrel®) and the Metformin-Etanercept (Product Name: Enbrel®) composite and at 3 days later, each cell was collected and reacted with an ROS antibody with a FITC wavelength range, and then, was measured using fluorescence activated cell sorting (FACs).

As a result, it was identified that the ROS was considerably inhibited by the Metformin-Etanercept (Product Name: Enbrel®) composite while no effects of ROS inhibition were observed in the groups treated solely with Etanercept (Product Name: Enbrel®) and Metformin (see FIG. 5).

Therefore, from the result of Example 4 and Example 5, it was known that the Metformin-Etanercept (Product Name: Enbrel®) composite was also effective for the autoimmune diseases including an inflammatory bowel disease.

Example 6

Figure 6A:
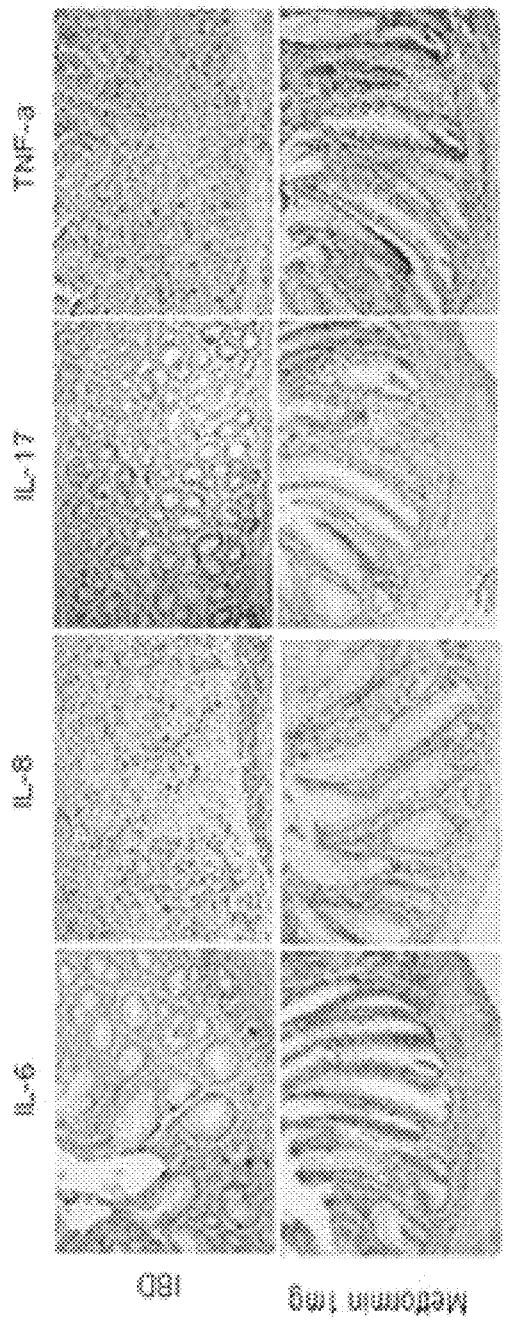
FIGS. 6A-6B illustrate the results of measuring the inflammatory cytokine regulations caused by Metformin in the colorectal tissues and colorectal cells of the group with an inflammatory bowel disease.
Figure 6B:
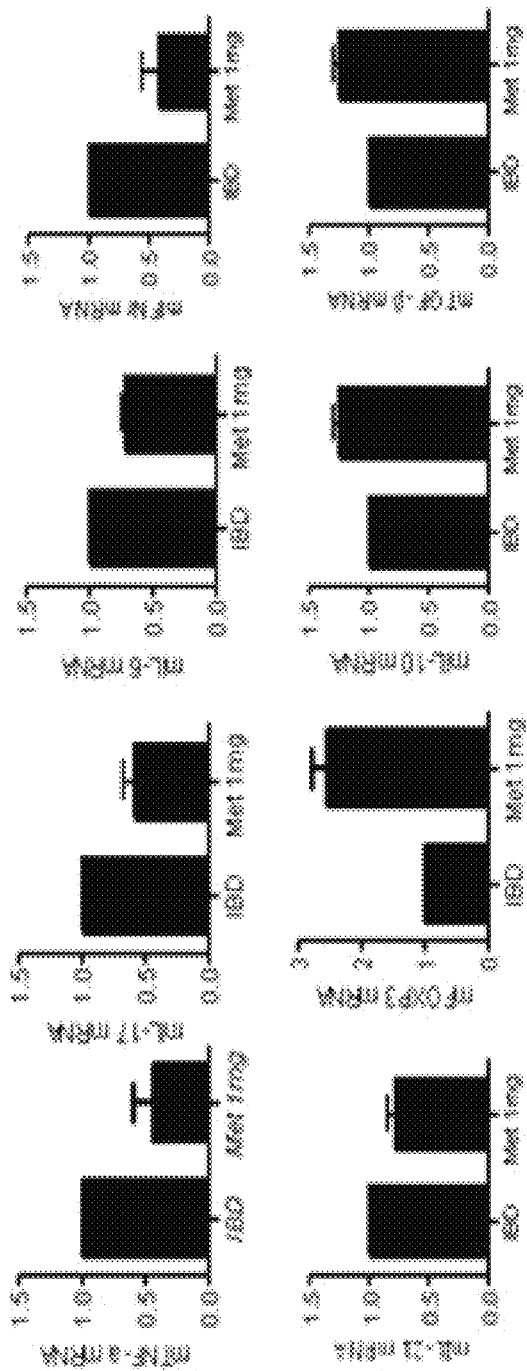
Figure 7:
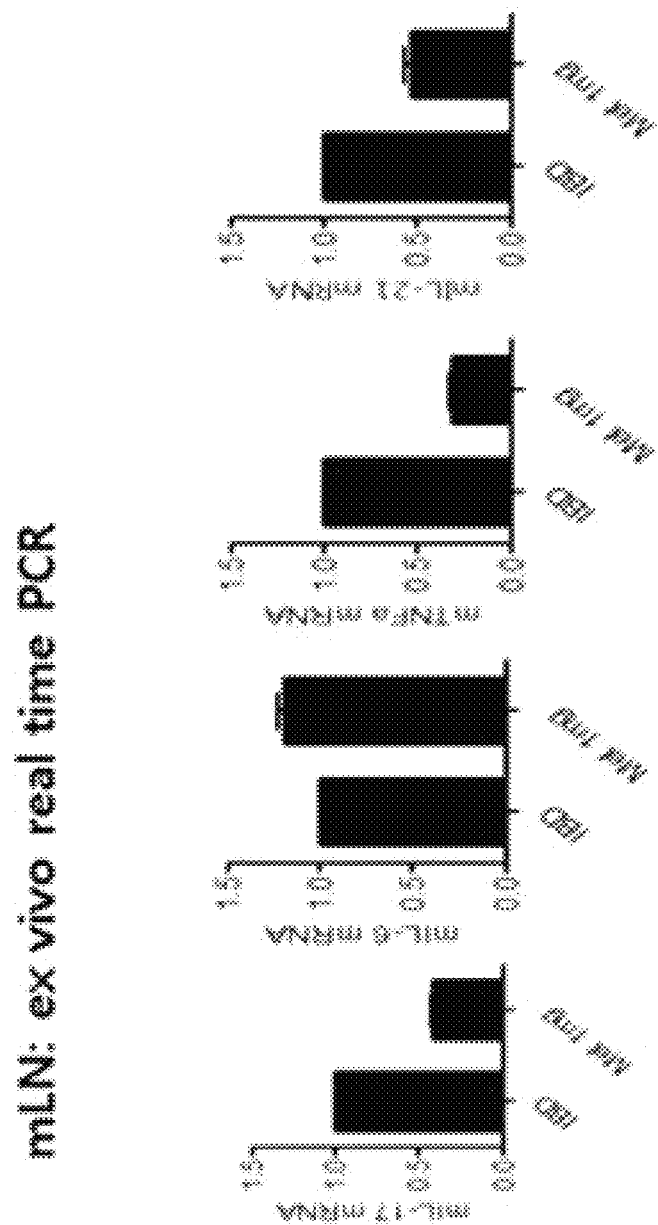
FIG. 7 illustrates the result of measuring the inflammatory cytokine regulations caused by Metformin in the lymph node tissues and cells of the group with an inflammatory bowel disease.

Analysis of Expression of Inflammatory Cytokine in Large Intestine of Mouse Injected with Metformin The inflammatory cytokines expressed in the colorectal tissues of an animal mouse injected with Metformin were studied and from histological findings, the considerable decrease in the expressions of IL-6, IL-8, IL-17, and TNF-α, the major inflammatory cytokine was observed. Moreover, from the study of gene expressions for the inflammatory cytokines in the cells of the large intestine, the expressions of the inflammatory cytokines were considerably inhibited as it was the case in the histological findings. Furthermore, the expressions of the inflammatory cytokine IL-10 and TGF-b were increased by Metformin. Foxp3, which was a regulatory T cell factor, was also increased (see FIG. 6).

Example 7

Analysis of Expression of Inflammatory Cytokine in Lymph Node of Mouse Injected with Metformin The inflammatory cytokines expressed in the lymph node of the animal mouse injected with Metformin were studied and the considerable decreases in the gene expressions of IL-17, IL-6, TNF-α, and IL-21, the major inflammatory cytokine were observed.

Example 8

Figure 8:
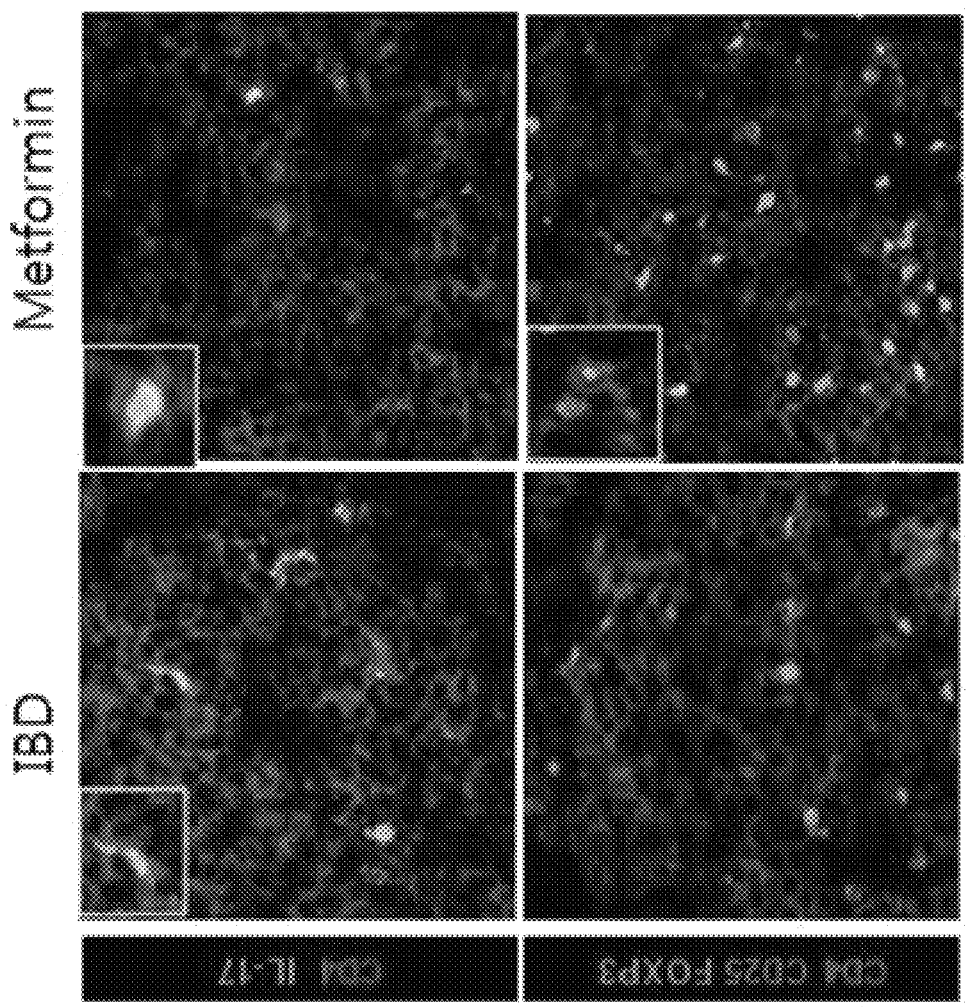
FIG. 8 illustrates the results exhibiting the effects of Metformin on a Treg/Th17 cell regulation in the spleen tissues of the group with an inflammatory bowel disease.

Analysis of Th17 Cells and Regulatory Treg Cells in Spleen of Mouse Injected with Metformin The expressions of Th17 cell and regulatory Treg cell in the spleen of the mouse injected with Metformin were studied using a confocal assay and the expressions of Th17 cells were considerably inhibited and the regulatory T cells that express Foxp3 were significantly increased (see FIG. 8).

Example 9

Analysis of Signaling Molecules in Spleen of Mouse Injected with Metformin

Figure 9:
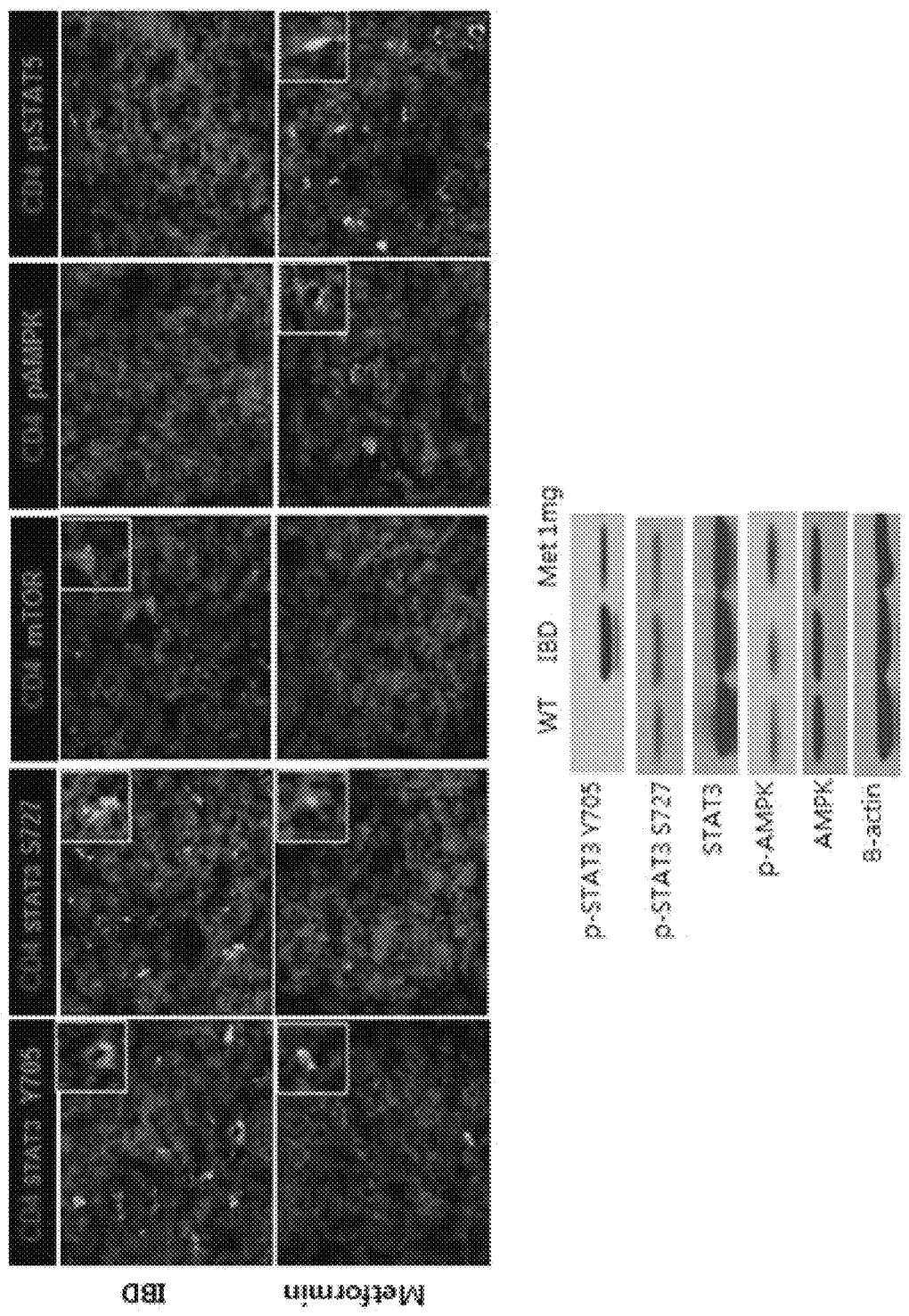
FIG. 9 illustrates the results exhibiting the p-STAT3, p-STAT5, and pAMPK regulations in the spleen tissues and cells of the group with an IBD.

In order to study signaling molecules regulated by Metformin in the spleen tissue of the animal mouse administered with Metformin, the tissue confocal was conducted and it was identified that the activities of STA3 and mTOR involved in the inflammation were considerably inhibited in the spleen cells injected with Metformin and the cells with the activated AMPK and STAT5 were increased. Even in the spleen cell proteins, the STAT3, 705, and 727 phosphorylated by Metformin were significantly inhibited, but the activated AMPK was increased (see FIG. 9).

Example 10

Figure 10:
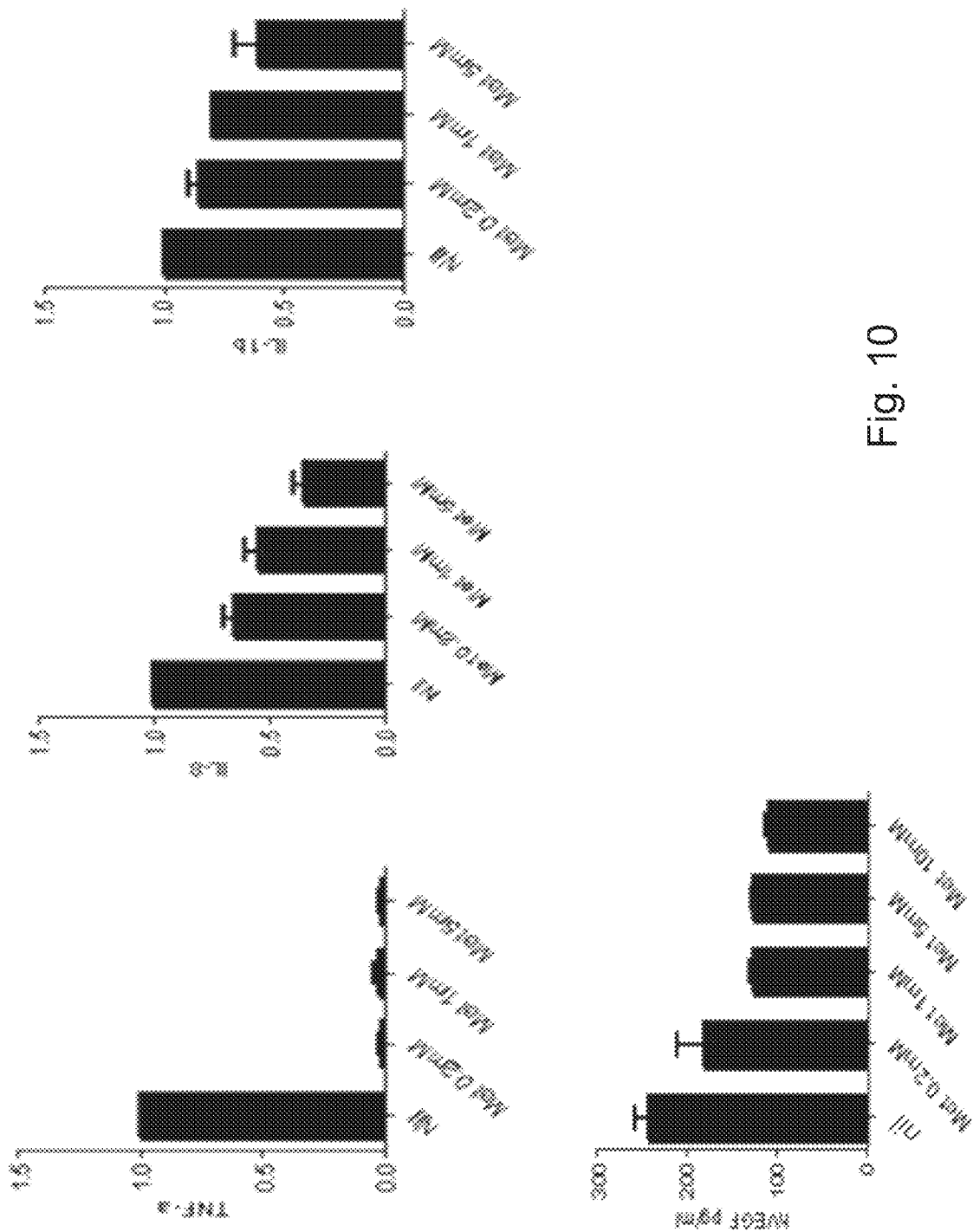
FIG. 10 illustrates the results exhibiting the effects of Metformin on the inflammatory cytokine regulations in a colon cancer cell line.

Analysis of Inflammatory Cytokine Inhibition by Metformin in Cell Line of Human Large Intestine The gene expressions of the inflammatory cytokines TNF-α, IL-8, and IL-1b were investigated after the cell line of human large intestine was treated with Metformin. The expressions of these inflammatory cytokines were inhibited in a Metformin concentration dependent manner (see FIG. 10).

Hitherto, the present invention was addressed mainly by the favorable exemplary embodiments thereof. An ordinary skill in the art to which the present invention belongs will understand that the present invention can be transformed and implemented without deviating from the essential properties thereof. Thus, all exemplary embodiments disclosed herein should be considered not in terms of limited aspects, but in terms of descriptive aspects. The scope of the present invention is not shown in the aforementioned description, but in the scope of request for a patent and all discrepancies existing in the equivalent scope should be regarded as included in the present invention.

The invention claimed is:

1. A method for treating inflammatory bowel disease, comprising administering to a subject having inflammatory bowel disease a therapeutically effective amount of a metformin compound of Formula 1

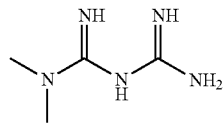

Formula 1 or a pharmaceutically acceptable salt thereof, in combination with a TNF-α inhibitor, wherein the TNF-α inhibitor is Etanercept.

2. The method of claim 1, wherein the inflammatory bowel disease is selected from the group consisting of Crohn's disease, intestinal lesions concomitant with Behcet's disease, ulcerative colitis, hemorrhagic rectal ulcer, and pouchitis.

* * * * *